(12) United States Patent
Vaccaro et al.

(10) Patent No.: US 7,216,544 B2
(45) Date of Patent: May 15, 2007

(54) ULTRASONIC INSPECTION REFERENCE STANDARD FOR COMPOSITE MATERIALS

(75) Inventors: Christopher M. Vaccaro, Ofallon, MO (US); David A. Lilienthal, Kent, WA (US)

(73) Assignee: The Boeing Company, Chicago, IL (US)

( * ) Notice: Subject to any disclaimer, the term of this patent is extended or adjusted under 35 U.S.C. 154(b) by 103 days.

(21) Appl. No.: 11/090,553

(22) Filed: Mar. 25, 2005

(65) Prior Publication Data

US 2006/0213250 A1    Sep. 28, 2006

(51) Int. Cl.
   G01N 33/44     (2006.01)
   G01N 29/30     (2006.01)
   C21C 14/54     (2006.01)

(52) U.S. Cl. ............... 73/620; 73/1.03; 204/192.13
(58) Field of Classification Search ............. 73/620, 73/623, 1.03, 1.86, 604; 204/192.11, 192.12, 204/298.02, 298.23, 298.07, 192.13
See application file for complete search history.

(56) References Cited

U.S. PATENT DOCUMENTS

| | | | | |
|---|---|---|---|---|
| 4,779,452 A | * | 10/1988 | Cohen-Tenoudji et al. | 73/54.41 |
| 5,064,520 A | * | 11/1991 | Miyake et al. | 204/192.11 |
| RE33,789 E | * | 1/1992 | Stevenson | 250/341.7 |
| 5,163,027 A | * | 11/1992 | Miller et al. | 367/13 |
| 6,843,945 B1 | * | 1/2005 | Lee et al. | 264/49 |
| 6,925,145 B2 | * | 8/2005 | Batzinger et al. | 378/59 |
| 7,076,992 B2 | * | 7/2006 | Greelish | 73/1.86 |

* cited by examiner

*Primary Examiner*—Hezron Williams
*Assistant Examiner*—Jacques M. Saint-Surin
(74) *Attorney, Agent, or Firm*—Ingrassia Fisher & Lorenz, P.C.

(57) ABSTRACT

An ultrasonic inspection reference standard for composite materials includes a prism that is manufactured from a polymer resin. The ultrasonic inspection reference standard may be a rectangular prism and may be a polymer resin step-wedge reference standard that has similar acoustic properties as prior art fiber-reinforced composite step-wedge reference standards at significantly lower manufacturing cost. A photo-polymer resin reference standard may be created using a stereo lithography process. The polymer resin reference standard may replace a currently used expensive fiber-reinforced composite reference standard. The ultrasonic inspection reference standard manufactured from a polymer resin may be used, for example, for ultrasonic inspection of fiber-reinforced composite parts. The polymer resin reference standard may be used, for example, in the aircraft airframe industry, both commercial and defense.

32 Claims, 3 Drawing Sheets

ULTRASONIC INSPECTION REFERENCE STANDARD FOR COMPOSITE MATERIALS

BACKGROUND OF THE INVENTION

The present invention generally relates to reference standards and ultrasonic inspection methods and, more particularly, to an ultrasonic inspection reference standard for composite materials and to an ultrasonic inspection process using a polymer resin reference standard.

The use of fiber-reinforced composite materials over metals and their alloys has increased significantly over the past years because of the weight savings and the improvement in fatigue life and corrosion control. Fiber-reinforced composite materials contain a strong and stiff fiber, such as a carbon fiber, embedded in a softer matrix material, such as a resin. The resin is used as a binding agent to hold the fibers together while the fibers provide the strength. The fibers can take on several forms including, for example, tape, fabric, and may be woven in either two dimensions or three dimensions. Laminated composite materials generally exhibit an initial stiffness that is used in the design of structures. Laminated composites are constructed of many layers of fiber-reinforced materials. Fiber-reinforced polymer matrix composites, such as graphite/epoxy and carbon/cyanate ester are now the materials of choice for spacecraft and launch vehicle structures and subsystems such as optical benches, instruments, and antennas. Furthermore, fiber-reinforced polymer matrix composites are widely used, for example, in commercial and military aircraft, sports equipment, and industrial and medical equipment.

The laminated composite materials undergo non-destructive testing procedures, such as ultrasonic and radiographic inspection, during aircraft manufacturing, maintenance, and repair. Common aircraft applications include thickness testing, delamination detection, and porosity evaluation of aircraft structures. Ultrasonic testing introduces high frequency sound waves into the test material to detect subsurface discontinuities. Transducers are used both to transmit and receive sound energy into and from test material. In the process, high frequency sound in the order of 500 KHz (kilohertz) to 10.0 MHz is sent, for example, into a composite laminate and echoes from the laminate are then measured in the time domain and the amplitude domain to determine the materials quality. Through-transmission and pulse-echo techniques are most commonly used in the aircraft airframe industry, both commercial and defense. The through-transmission technique uses a sending transducer that introduces the ultrasonic energy into the test part and a receiving transducer that measures the amount of energy that exits the part at the opposite side. The amount of energy absorbed is then evaluated. The pulse-echo technique uses only one transducer that introduces short bursts of ultrasonic energy into the test part at regular intervals and that also measures the amount of energy that is reflected from an internal flaw or structural discontinuities as well as the time delay between transmission of the initial pulse and the arrival of the echo. The amount of energy reflected is a function of the size of the flaw in relation to the size of the incident beam. Some advantages of the ultrasonic testing method include high penetrating capability, high sensitivity and resolution, portability, single surface accessibility, and the immediate interpretation of test results. Reference standards are required to calibrate the test equipment to ensure the successful operation of the test equipment.

Composite reference standards are employed when performing ultrasonic inspection to establish the bulk attenuation properties for a pristine material. Typical composite standards are manufactured using fiber-reinforced resins identical to the materials used in the final product and, therefore, in the parts to be tested. The cost of building a composite reference standard include, for example, the cost to design, material cost, labor cost to lay-up the material, autoclave usage cost, post-cure machining cost and the standard qualification cost. For example, the preparation of photomicrographs, image analysis, and acid digestion, a process of dissolving material in an acid matrix that may be used for laboratory analysis, may be reflected in the standard qualification cost. Furthermore, some resin systems also require an additional cure process whereby the material returns to the oven or autoclave after its initial cure to advance the cure state of the resin. Therefore, composite reference standards are undesirable due to the cost to design, manufacture, and qualify. A typical step-wedge standard that is commonly used, for example, during the ultrasonic inspection of airframes, costs between about $2,000 and about $4,000.

As can be seen, there is a need for an alternative approach to building composite reference standards to reduce the cost of design, manufacturing, and qualification. Furthermore, there is a need for a method that enables the mass production of reference standards that can be used for ultrasonic inspection of composite materials due to the growing industrial application of composite materials and, therefore, an increased volume of composite parts to be inspected using ultrasonic inspection techniques.

There has, therefore, arisen a need to provide a reference standard that can be used in ultrasonic inspection processes for composite materials, that is inexpensive, that may be produced in high quantities, and that can replace existing expensive composite standards. There has further arisen a need to manufacture a standard for ultrasonic inspection of composite materials that has acoustic properties that are comparable to currently existing composite standards but can be manufactured at a lower cost and with a reduced machining time.

SUMMARY OF THE INVENTION

The present invention provides an ultrasonic inspection reference standard for composite materials. The present invention provides a fiber-free polymer resin step-wedge reference standard that has similar acoustic properties as prior art fiber-reinforced composite step-wedge reference standards but has significantly lower manufacturing cost. The present invention provides a polymer resin reference standard that is suitable for, but not limited to, ultrasonic inspection of laminated composite parts used in the aircraft airframe industry, both commercial and defense.

In one aspect of the present invention, an ultrasonic inspection reference standard for composite materials comprises a rectangular prism having a thickness. The rectangular prism is manufactured from a fiber-free polymer resin.

In another aspect of the present invention, an ultrasonic inspection reference standard for composite materials comprises a step-wedge having a first thickness at a first end and a second thickness at a second end. The first thickness is larger than the second thickness. The step-wedge includes a plurality of steps each step having a height. The step at the first end has the largest height and the step at the second end has the smallest height. The height of the steps decreases from the first end to the second end. The step-wedge is manufactured from a fiber-free polymer resin.

In a further aspect of the present invention, an ultrasonic inspection process for composite materials comprises the steps of: manufacturing an ultrasonic inspection reference standard from a fiber-free polymer resin; and inspecting the fiber-reinforced composite part using an ultrasonic technique using said fiber-free polymer resin reference standard.

These and other features, aspects and advantages of the present invention will become better understood with reference to the following drawings, description and claims.

DETAILED DESCRIPTION OF THE INVENTION

Figure 1:
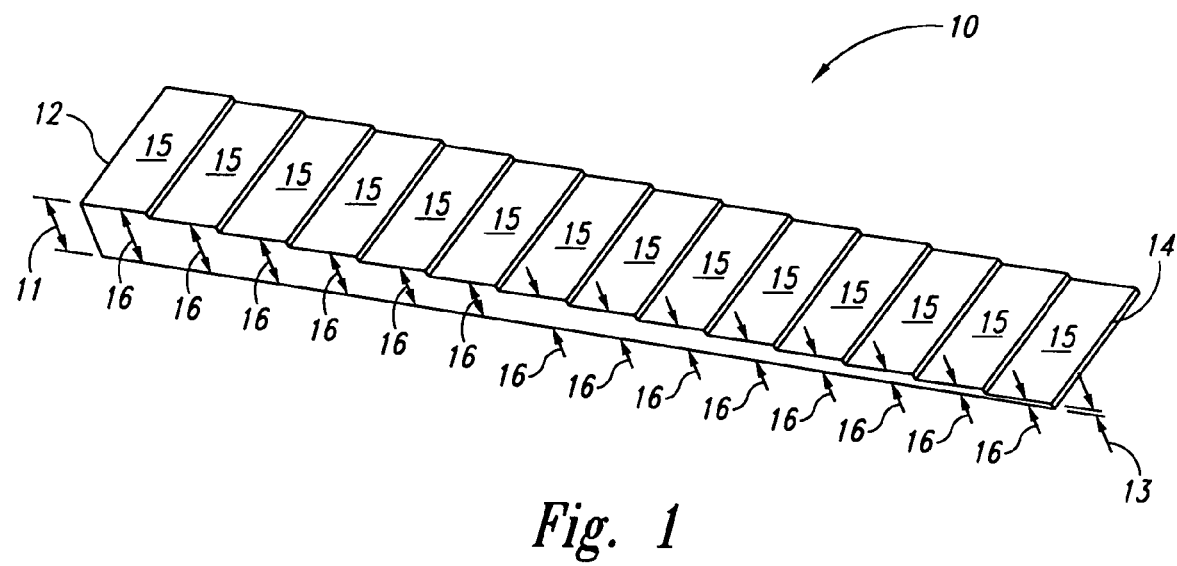
FIG. 1 is a perspective view of an ultrasonic inspection reference standard for composite materials according to one embodiment of the present invention.

The following detailed description is of the best currently contemplated modes of carrying out the invention. The description is not to be taken in a limiting sense, but is made merely for the purpose of illustrating the general principles of the invention, since, the scope of the invention is best defined by the appended claims.

Broadly, the present invention provides an ultrasonic inspection reference standard for composite materials. In one embodiment the present invention provides a fiber-free polymer resin step-wedge reference standard that provides similar acoustic properties as prior art fiber-reinforced composite step-wedge reference standards at significantly lower manufacturing cost. An embodiment of the present invention provides a polymer resin step-wedge reference standard that is suitable for, but not limited to, ultrasonic inspection of composite parts used in the aircraft airframe industry, both commercial and defense.

In one embodiment, the present invention provides a fiber-free photo-polymer resin reference standard that may be used during ultrasonic inspection of fiber-reinforced composite materials, such as composite laminates. The photo-polymer resin reference standard as in one embodiment of the present invention has similar acoustic properties as a prior art composite reference standard that is manufactured from the same material as the part to be inspected, such as graphite/epoxy. Contrary to prior art composite reference standards, the photo-polymer resin reference standard as in one embodiment of the present invention can be manufactured at a significantly lower cost. By using a polymer resin that is free of fibers for the reference standard as in one embodiment of the present invention instead of using the fiber-reinforced composite material, which is resin with fiber, as done in the prior art, the cost and time for design, manufacture, and qualification of a reference standard for ultrasonic inspection of composite materials can be reduced while the acoustic properties of the composite material to be tested can be mimicked. Since the fiber provides strength for the composite material but does not influences the acoustic properties of the composite material significantly, it may be possible to manufacture a reference standard by using only the polymer resin of the composite to be tested as in one embodiment of the present invention to achieve acoustic properties that are similar to the acoustic properties of the fiber-reinforced composite reference standard. Consequently, it may be possible to replace the prior art fiber-reinforced composite reference standard with the fiber-free polymer resin reference standard as in one embodiment of the present invention. Furthermore, it may be possible as in one embodiment of the present invention to achieve acoustic properties that are comparable to the acoustic properties of a composite reference standard even if the polymer resin used does not match the resin used in the composite to be inspected. For example, the acoustic properties of a photo-polymer resin step-wedge reference standard as in one embodiment of the present invention may be similar enough to acoustic properties of a prior art graphite/epoxy step-wedge reference standard to replace the expensive prior art step-wedge standard.

In one embodiment, the present invention utilizes a stereo lithography process that can also be used, for example, for rapid prototyping, to manufacture photo-polymer resin reference standards with varying thickness and geometries that closely resemble the part under inspection. By using the stereo lithography process to create a polymer resin reference standard for ultrasonic testing of fiber-reinforced composite materials as in one embodiment of the present invention the lay-up and machining time needed may be significantly reduced compared to the lay-up and machining time needed to produce a prior art composite reference standard. Furthermore, using the stereo lithography process to create a polymer resin reference standard as in one embodiment of the present invention may enable production of reference standards in higher quantities and may enable faster realization of new reference standard designs than currently possible. The stereo lithography process also enables the creation of photo-polymer resin reference standards according to one embodiment of the present invention with added versatility of geometry control compared to the manufacturing process for prior art fiber-reinforced composite reference standards.

Figure 2:
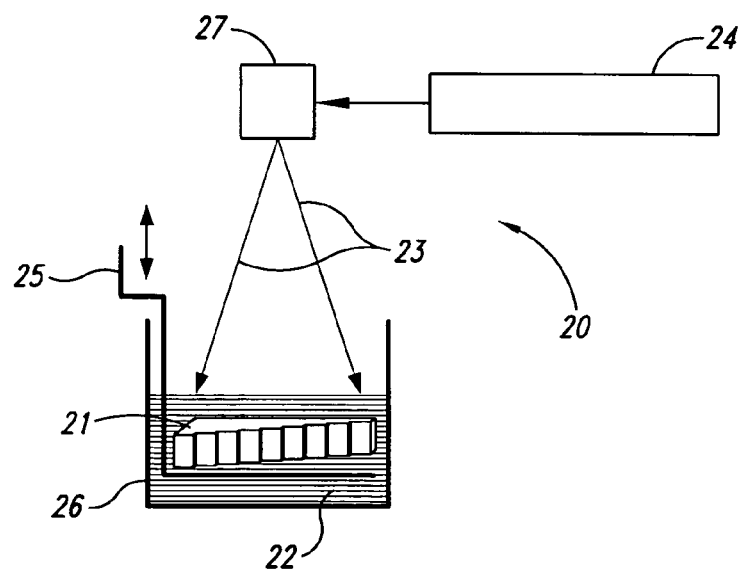
FIG. 2 is a front view of a stereo lithography process according to one embodiment of the present invention.

Referring now to FIG. 1, an ultrasonic inspection reference standard 10 for composite materials is illustrated according to one embodiment of the present invention. The ultrasonic inspection reference standard 10 may have the shape of a rectangular prism having a thickness 11. The ultrasonic inspection reference standard 10 may further be a step-wedge having the shape of a wedge that may be shaped like a narrow V in cross section. The ultrasonic inspection reference standard 10 may have a first thickness 11 at a first end 12 and a second thickness 13 at a second end 14. The first thickness 11 may be larger than the second thickness 13. The ultrasonic inspection reference standard 10 may further include a plurality of steps 15. Each step 15 may have a height 16 such that the step 15 at the first end 12 may have the largest height 16, such that the step 15 at the second end 13 may have the smallest height 16, and such that the height 16 of the steps 15 decreases from the first end 12 to the second end 14, as illustrated in FIG. 2. The height 16 of the steps 15 may decrease by the same amount from step 15 to step 15 from the first end 12 to the second end 14. The ultrasonic inspection reference standard 10 may be a step-wedge standard as shown in FIG. 1. The number of steps 15 as well as the height 16 of the steps 15 may be variable and may depend on the inspection task. The ultrasonic inspection reference standard 10 may be manufactured from a fiber-free polymer resin, such as a photo-polymer resin or a cast resin. The fiber-free polymer resin of the reference standard 10 may be selected independently from the resin used in the composite to be tested. The ultrasonic inspection reference standard 10 may further be manufactured from the same resin as used in the fiber-reinforced composite material to be inspected using ultrasonic techniques, for example, if a part to be inspected is manufactured from graphite/epoxy, the ultrasonic inspection reference standard 10 may be manufactured from epoxy. The ultrasonic inspection reference standard 10 manufactured from a fiber-free polymer resin may have the same dimensions, for example, as a prior art step-wedge standard manufactured from a fiber-reinforced composite material. The ultrasonic inspection reference standard 10 may further have a geometry that closely resembles a fiber-reinforced composite part to be inspected.

The ultrasonic inspection reference standard 10 may be manufactured using a stereo lithography process 20 as shown in FIG. 2. The stereo lithography process 20, as illustrated in FIG. 2, may produce plastic parts 21, such as the ultrasonic inspection reference standard 10, directly from a 3D CAD (computer-aided design) model. The surface of a liquid photopolymer 22 is solidified layer-by-layer using a laser beam 23 emitted by a laser 24. When the laser beam 23 hits the liquid photopolymer 22, it solidifies the resin. When a layer is fully traced, a movable table 25 is than lowered in the vat 26. A scanner system 27 directs the laser beam 23 according to a loaded CAD model. The self-adhesive property of the material causes the layers to stick with each other and in this way a three-dimensional part 21 is formed in multi-layers. The stereo lithography process 20 is very accurate and suitable for smooth surface finished parts. Parts manufactured using the stereo lithography process 20 may be used, for example, for conceptual designs, product verification, pattern making. The stereo lithography process 20 may be used, for example, for rapid prototyping. If the reference standard 10 were manufactured using the stereo lithography process 20 as shown in FIG. 2, the reference standard 10 would be manufactured from a photo-polymer resin. Using the stereo lithography process 20 may further enable to manufacture ultrasonic inspection reference standards, such as the polymer resin reference standard 10, with a varying thickness and with geometries that resemble the fiber-reinforced part to be inspected. It may further be possible to use a resin that can be casted to manufacture the reference standard 10. Such resin may be preferably the same resin as used in the fiber-reinforced composite part to be tested. Casting a resin may include the steps of building a mold, pouring a cast resin into the mold, and baking the resin at cure temperature. Both methods to manufacture the ultrasonic inspection reference standard 10 from a fiber-free polymer resin may not require any tooling. Manufacturing the ultrasonic inspection reference standard 10 may not be limited to the above-mentioned methods.

Figure 3:
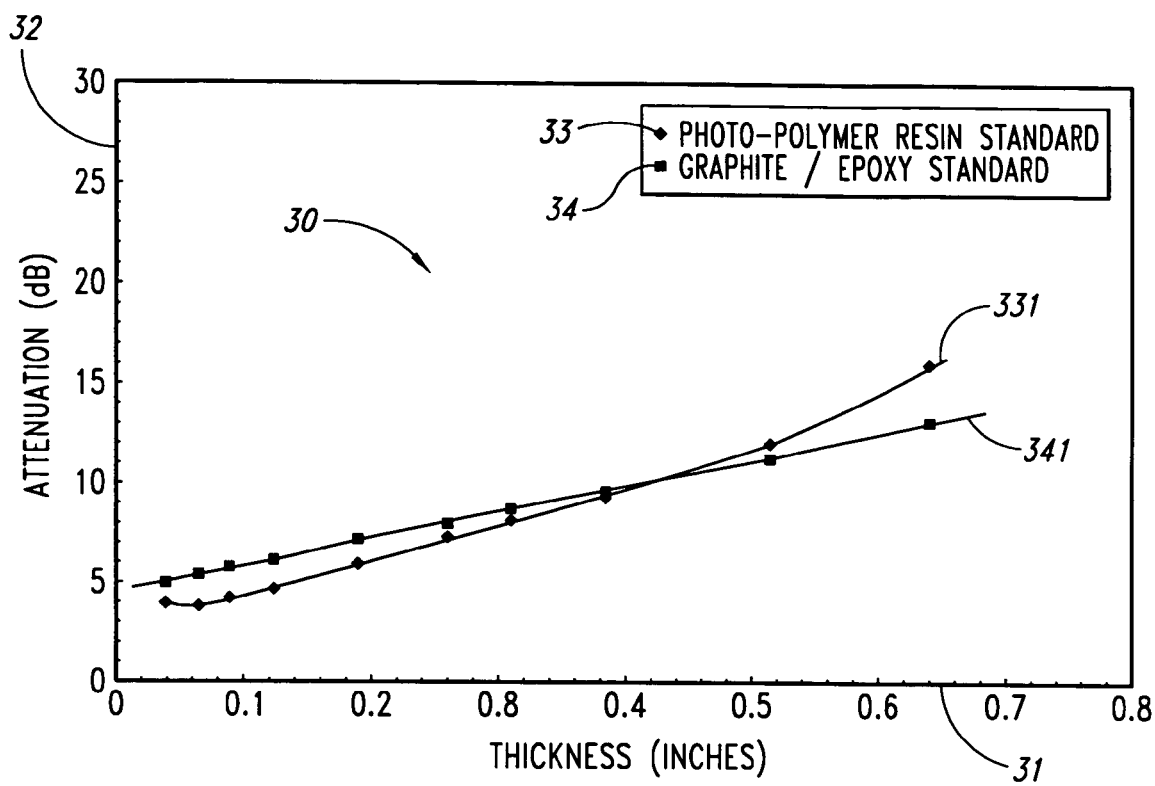
FIG. 3 is an x-y plot showing attenuation vs. thickness for through-transmission technique according to one embodiment of the present invention.

Referring now to FIG. 3, an x-y plot 30 showing attenuation vs. thickness for through-transmission technique is illustrated according to one embodiment of the present invention. The plot 30 may include an x-axis 31 showing the thickness, such as the thickness 11 and 13, of the ultrasonic inspection reference standard 10 at each step 15 measured in inches. The plot 30 may further include a y-axis 32 showing the attenuation measured in decibel (dB). The attenuation is a decrease in intensity of a sound wave as a result of absorption of energy and of scattering out of the path of a receiving transducer. The plot 30 may further include data points 33 obtained with ultrasonic through-transmission for a photo-polymer resin step-wedge reference standard 10, as illustrated in FIG. 1, that is free of fibers. The plot 30 may further include data points 34 obtained with ultrasonic through-transmission for a prior art graphite/epoxy reference standard. To demonstrate the use of a fiber-free photo-polymer resin as a reference standard, a photo-polymer resin step-wedge reference standard 10 (shown in FIG. 1) was manufactured with the same physical steps as a prior art graphite/epoxy step-wedge reference standard by using the stereo lithography process 20 (shown in FIG. 2). Both standards were then ultrasonically scanned at 5.0 MHz using the through-transmission technique. The obtained data are illustrated in the plot 30 shown in FIG. 3.

Figure 4:
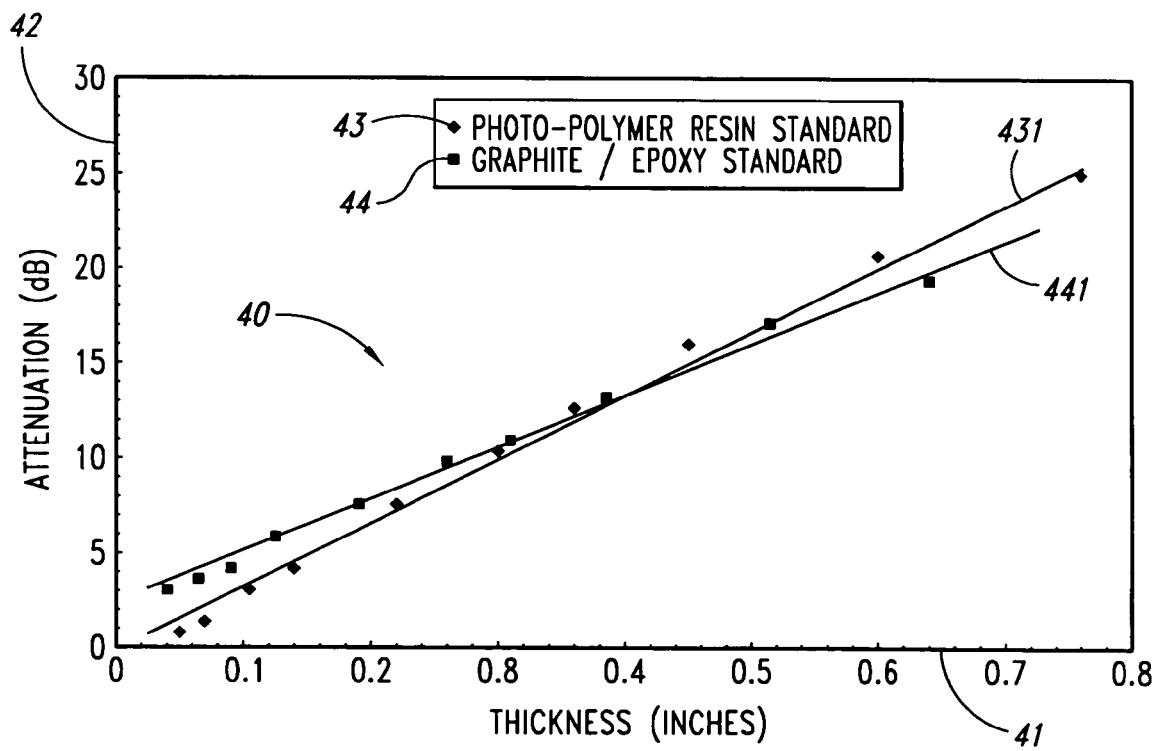
FIG. 4 is an x-y plot showing attenuation vs. thickness for pulse-echo technique according to one embodiment of the present invention.

Referring now to FIG. 4, an x-y plot 40 showing attenuation vs. thickness for pulse-echo technique is illustrated according to one embodiment of the present invention. The plot 40 may include an x-axis 41 showing the thickness, such as the thickness 11 and 13, of the ultrasonic inspection reference standard 10 at each step 15 measured in inches. The plot 40 may further include a y-axis 42 showing the attenuation measured in decibel (dB). The attenuation is a decrease in intensity of a sound wave as a result of absorption of energy and of scattering out of the path of a receiving transducer. The plot 40 may further include data points 43 obtained in ultrasonic pulse-echo mode for a photo-polymer resin step-wedge reference standard 10, as illustrated in FIG. 1, that is free of fibers. The plot 40 may further include data points 44 obtained with ultrasonic through-transmission for a prior art graphite/epoxy reference standard. To demonstrate the use of a fiber-free photo-polymer resin as a reference standard, a photo-polymer resin step-wedge reference standard 10 (shown in FIG. 1) was manufactured with the same physical steps as a prior art step-wedge graphite/epoxy reference standard by using the stereo lithography process 20 (shown in FIG. 2). Both standards were then ultrasonically scanned at 5.0 MHz using the pulse-echo technique. The obtained data are illustrated in the plot 40 shown in FIG. 4.

As can be seen in FIGS. 3 and 4, the slope (331 and 431, respectively) of the photo-polymer resin standard 10 is steeper than the slope (341 and 441, respectively) of the prior art graphite/epoxy reference standard. However, the results are within the system noise, which is typically +/−2 dB. Consequently, the prior art graphite/epoxy reference standard may be substituted with the photo-polymer resin reference standard 10 (shown in FIG. 1) that is fiber-free as in one embodiment of the present invention. Since ultrasonic attenuation is material dependent, altering the thickness, such as 11 and 13, of the polymer resin reference standard 10, for example, by adjusting the height 16 of the steps 15 may be used to bring the slopes (331 and 341, 431 and 441) in line if needed. Using this approach, a fiber-free polymer resin reference standard 10 may be designed to have an equivalent thickness based on the material properties of the fiber-reinforced composite part to be tested and not the actual thickness of a prior art fiber-reinforced composite reference standard.

Figure 5:
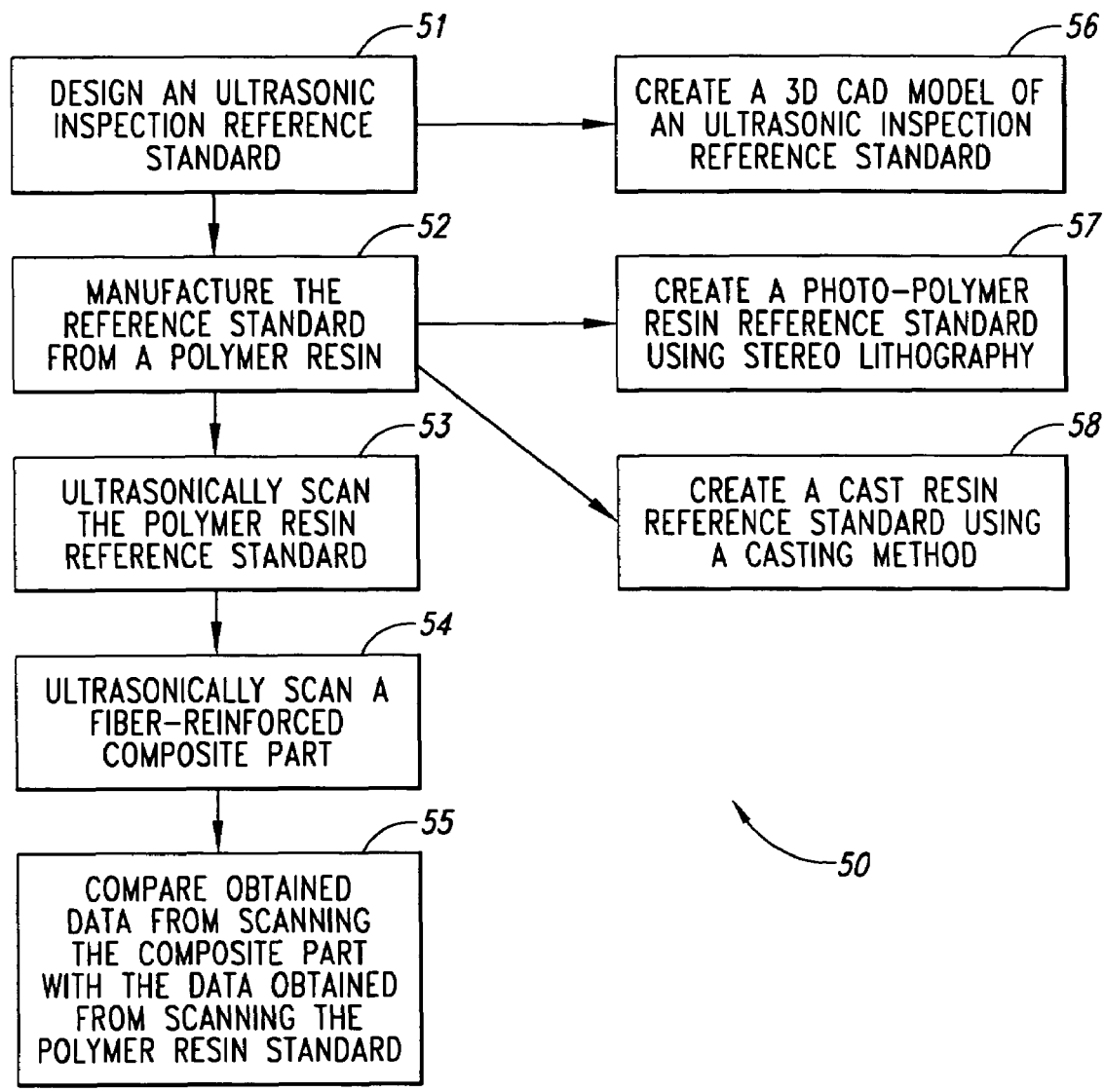
FIG. 5 is a flow chart of an ultrasonic inspection process for composite materials according to another embodiment of the present invention.

Referring now to FIG. 5, an ultrasonic inspection process for composite materials 50 is illustrated according to another embodiment of the present invention. The ultrasonic inspection process 50 may include the steps of: designing an ultrasonic inspection reference standard 10 according to a fiber-reinforced composite part to be inspected in step 51, manufacturing the reference standard 10 from a fiber-free polymer resin in step 52, ultrasonically scanning the polymer resin reference standard 10 using an ultrasonic inspection technique, such as pulse-echo and through-transmission technique in step 53, ultrasonically scanning a fiber-reinforced composite part in step 54, and comparing the obtained data from scanning the composite part with the data obtained from scanning the polymer resin reference standard 10 in step 55. Designing the ultrasonic inspection reference standard 10 (step 51) may include creating a 3D CAD model in step 56. The fiber-free polymer resin reference standard 10 may be manufactured, for example, as in steps 57 or 58. A photo-polymer resin reference standard 10 may be manufactured by using the prior art stereo lithography process 20 (step 57). A cast resin reference standard may be manufactured by using a casting method in step 58. By using a fiber-free polymer resin (step 52) to manufacture an ultrasonic inspection reference standard, such as the reference standard 10, the reference standard may be manufactured at significantly lower manufacturing cost and time compared to existing fiber-reinforced composite reference standards, while providing similar acoustic properties.

It should be understood, of course, that the foregoing relates to exemplary embodiments of the invention and that modifications may be made without departing from the spirit and scope of the invention as set forth in the following claims.

We claim:

1. An ultrasonic inspection reference standard for composite materials, the ultrasonic inspection reference standard comprising:
    a first surface;
    a second surface disposed perpendicular to said first surface and having a thickness, wherein said first surface and said second surface are configured such that the ultrasonic inspection reference standard is a prism;
    wherein the prism is manufactured from a fiber-free polymer resin and is configured such that it has an acoustic property that can be compared to an acoustic property of a composite material part during ultrasonic inspection to determine structural characteristics of said composite material part.

2. The ultrasonic inspection reference standard for composite materials of claim 1, wherein said polymer resin is a photo-polymer resin.

3. The ultrasonic inspection reference standard for composite materials of claim 1, wherein said polymer resin is a cast resin.

4. The ultrasonic inspection reference standard for composite material of claim 1, wherein said polymer resin is identical to a resin of said composite material part to be inspected.

5. The ultrasonic inspection reference standard for composite materials of claim 1, wherein said prism is a step-wedge having a first thickness at a first end and a second thickness at a second end, wherein said first thickness is larger than said second thickness, wherein said step-wedge includes a plurality of steps with each step having a height, wherein a first step at said first end has the largest height, wherein a second step at said second end has the smallest height, and wherein said heights of said steps decrease from said first end to said second end.

6. The ultrasonic inspection reference standard for composite materials of claim 1, wherein said thickness is an equivalent thickness based on material properties of said composite material part to be inspected.

7. The ultrasonic inspection reference standard for composite materials of claim 1, wherein said prism is manufactured using a stereo lithography process.

8. The ultrasonic inspection reference standard for composite materials of claim 1, wherein said prism is manufactured by casting.

9. The ultrasonic inspection reference standard for composite materials of claim 1, wherein said prism is a rectangular prism.

10. An ultrasonic inspection reference standard for composite materials, comprising:
    a step-wedge having a first thickness at a first end and a second thickness at a second end, wherein said first thickness is larger than said second thickness, wherein said step-wedge includes a plurality of steps each step having a height, wherein said step at said first end has the largest height, wherein said step at said second end has the smallest height, and wherein said height of said steps decreases from said first end to said second end; and
    wherein said step-wedge is manufactured from a fiber-free polymer resin.

11. The ultrasonic inspection reference standard for composite materials of claim 10, wherein said height of said steps decreases by the same amount at each step from said first end to said second end.

12. The ultrasonic inspection reference standard for composite materials of claim 10, wherein said height of said steps of said step-wedge manufactured from a polymer resin is an equivalent height based on material properties of a composite material to be inspected.

13. The ultrasonic inspection reference standard for composite materials of claim 10, wherein said height of said steps of said polymer resin step-wedge is identical to the height of steps of a graphite/epoxy step-wedge reference standard.

14. The ultrasonic inspection reference standard for composite materials of claim 13, wherein acoustic properties of said polymer resin step-wedge are similar to acoustic properties of said graphite/epoxy step-wedge reference standard.

15. The ultrasonic inspection reference standard for composite materials of claim 13, wherein said polymer resin step-wedge replaces said graphite/epoxy step-wedge reference standard.

16. The ultrasonic inspection reference standard for composite materials of claim 10, wherein said step-wedge is manufactured from a photo-polymer resin using a stereo lithography process.

17. The ultrasonic inspection reference standard for composite materials of claim 10, wherein said step-wedge is manufactured from a cast resin by casting.

18. The ultrasonic inspection reference standard for composite materials of claim 10, wherein said step-wedge is used to inspect fiber-reinforced composite parts of an aircraft airframe.

19. An ultrasonic inspection process for composite materials, comprising the steps of:
    manufacturing an ultrasonic inspection reference standard from a fiber-free polymer resin; and
    inspecting a fiber-reinforced composite part with an ultrasonic technique using said fiber-free polymer resin reference standard.

20. The ultrasonic inspection process for composite materials of claim 19, further comprising the steps of:
    ultrasonically scanning said fiber-free polymer resin reference standard using an ultrasonic inspection technique;
    ultrasonically scanning said fiber-reinforced composite part using said ultrasonic inspection technique; and comparing data obtained from scanning said fiber-reinforced composite part with data obtained from scanning said fiber-free polymer resin reference standard.

21. The ultrasonic inspection process for composite materials of claim 19, further comprising the steps of:
   creating a 3D CAD model of an ultrasonic inspection standard; and
   creating a photo-polymer resin reference standard using stereo lithography.

22. The ultrasonic inspection process for composite materials of claim 19, further comprising the steps of:
   building a mold;
   pouring a cast resin into said mold; and
   baking said cast resin at cure temperature.

23. The ultrasonic inspection process for composite materials of claim 19, further comprising the step of using an ultrasonic technique selected from the group consisting of pulse-echo technique and through-transmission technique to scan said fiber-free polymer resin reference standard and said fiber-reinforced composite part.

24. The ultrasonic inspection process for composite materials of claim 19, further comprising the steps of:
   manufacturing a fiber-free photo-polymer resin step-wedge reference standard using a stereo lithography process; and
   replacing a fiber-reinforced composite step-wedge reference standard with said photo-polymer step-wedge reference standard.

25. The ultrasonic inspection process for composite materials of claim 24, further comprising the step of designing said fiber-free photo-polymer resin step-wedge reference standard to have an equivalent thickness that is different from a thickness of said fiber-reinforced composite step-wedge reference standard and that is based on material properties of said fiber-reinforced composite part.

26. A method for inspecting a composite material part, the method comprising the steps of:
   ultrasonically scanning a fiber-free polymer resin reference standard using an ultrasonic inspection technique;
   ultrasonically scanning the composite material part using the ultrasonic inspection technique; and
   comparing data obtained from scanning said fiber-free polymer resin reference standard with data obtained from scanning the composite material part.

27. The method of claim 26, wherein the steps of ultrasonically scanning are performed by using a pulse-echo technique or a through-transmission technique.

28. The method of claim 26, wherein the step of ultrasonically scanning a fiber-free polymer resin reference standard comprises the step of ultrasonically scanning a reference standard formed of a polymer resin that is substantially identical to a resin of the composite material part.

29. The method of claim 26, wherein the step of ultrasonically scanning a fiber-free polymer resin reference standard comprises the step of ultrasonically scanning a reference standard having a rectangular prism shape.

30. The method of claim 29, wherein the step of ultrasonically scanning a fiber-free polymer resin reference standard comprises the step of ultrasonically scanning a reference standard having a step-wedge shape, wherein the reference standard has a first thickness at a first end and a second thickness at a second end, wherein said first thickness is larger than said second thickness, wherein said reference standard has a plurality of steps that each has a height, wherein a first step at said first end has the largest height, wherein a second step at said second end has the smallest height, and wherein said heights of said steps decrease from said first end to said second end.

31. The method of claim 26, wherein the step of ultrasonically scanning a fiber-free polymer resin reference standard comprises the step of ultrasonically scanning a reference standard having a geometry that substantially resembles a geometry of the composite material part.

32. The ultrasonic inspection reference standard for composite materials of claim 1, wherein said prism has a geometry that substantially resembles a geometry of said composite material part to be inspected.

* * * * *